United States Patent
Kimmlingen

(10) Patent No.: US 11,340,327 B2
(45) Date of Patent: May 24, 2022

(54) COIL FACILITY FOR A MAGNETIC RESONANCE INSTALLATION AND MAGNETIC RESONANCE INSTALLATION

(71) Applicant: Siemens Healthcare GmbH, Erlangen (DE)

(72) Inventor: Ralph Kimmlingen, Zirndorf (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/881,756

(22) Filed: May 22, 2020

(65) Prior Publication Data

US 2020/0371186 A1 Nov. 26, 2020

(30) Foreign Application Priority Data

May 22, 2019 (DE) .......................... 102019207492.8

(51) Int. Cl.
*G01R 33/62* (2006.01)
*A61B 5/055* (2006.01)
(Continued)

(52) U.S. Cl.
CPC .............. *G01R 33/62* (2013.01); *A61B 5/055* (2013.01); *G01R 33/34076* (2013.01);
(Continued)

(58) Field of Classification Search
CPC .............. G01R 33/62; G01R 33/34076; G01R 33/3621; G01R 33/3628; G01R 33/3664;
(Continued)

(56) References Cited

U.S. PATENT DOCUMENTS 5,311,134 A * 5/1994 Yamagata .......... G01R 33/3858
324/318
5,928,148 A * 7/1999 Wang ..................... A61B 5/411
600/420

(Continued)

OTHER PUBLICATIONS

Avdievich, N. I., and H. P. Hetherington. "4 T Actively detuneable double-tuned 1H/31P head volume coil and four-channel 31P phased array for human brain spectroscopy." Journal of magnetic resonance 186.2 (2007): pp. 1-14.

(Continued)

*Primary Examiner* — Dixomara Vargas
(74) *Attorney, Agent, or Firm* — Lempia Summerfield Katz LLC

(57) ABSTRACT

A coil facility for a magnetic resonance installation and a magnetic resonance installation having such a coil facility are provided. The coil facility in this case includes a double-resonant transmit resonator for two frequencies and a first receiver and a second receiver, each for one of the two frequencies. The coil facility has an actuator system for effecting a relative spatial transposition of the transmit resonator, the first receiver, and the second receiver into various settings. In a first setting, only the first receiver, and in a second setting, only the second receiver, for receiving corresponding MR signals is arranged in an examination space that is at least sectionally surrounded by the transmit resonator.

20 Claims, 4 Drawing Sheets

(51) Int. Cl.
  *G01R 33/34* (2006.01)
  *G01R 33/36* (2006.01)
  *G01R 33/54* (2006.01)
  *G01R 33/561* (2006.01)
(52) U.S. Cl.
  CPC ..... *G01R 33/3621* (2013.01); *G01R 33/3628* (2013.01); *G01R 33/3664* (2013.01); *G01R 33/543* (2013.01); *G01R 33/5611* (2013.01)
(58) Field of Classification Search
  CPC .... G01R 33/543; G01R 33/5611; A61B 5/055
  See application file for complete search history.

(56) References Cited

U.S. PATENT DOCUMENTS

| | | | | |
|---|---|---|---|---|
| 6,586,934 B2* | 7/2003 | Biglieri | ............ | G01R 33/34046 324/307 |
| 7,218,106 B2* | 5/2007 | Yasuhara | ............ | G01R 33/341 324/307 |
| 7,330,030 B2* | 2/2008 | Nakabayashi | ..... | G01R 33/3415 324/309 |
| 7,525,311 B2* | 4/2009 | Steckner | ............ | G01R 33/3415 324/318 |
| 7,598,737 B2* | 10/2009 | Campagna | ......... | G01R 33/3415 324/307 |
| 7,696,752 B2* | 4/2010 | Takamori | ............ | G01R 33/3415 324/307 |
| 8,560,051 B2* | 10/2013 | Piron | .................... | A61B 90/11 600/411 |
| 9,241,765 B2* | 1/2016 | Piron | .................... | A61B 8/4416 |
| 2008/0211495 A1* | 9/2008 | Steckner | .......... | G01R 33/34084 324/300 |
| 2010/0301862 A1* | 12/2010 | Tropp | ................ | G01R 33/3415 324/318 |
| 2011/0210735 A1* | 9/2011 | Trakic | .................. | G01R 33/422 324/309 |
| 2013/0307535 A1* | 11/2013 | Taracila | ............ | G01R 33/3415 324/307 |
| 2013/0307540 A1* | 11/2013 | Taracila | ............... | G01R 33/481 324/318 |
| 2016/0161577 A1* | 6/2016 | Taracila | ........... | G01R 33/34084 324/309 |
| 2018/0024206 A1* | 1/2018 | Heismann | ........ | G01R 33/34007 324/309 |

OTHER PUBLICATIONS

German Office Action for German Application No. 10 2019 207 492.8 dated Mar. 12, 2020.

* cited by examiner

FIG 1

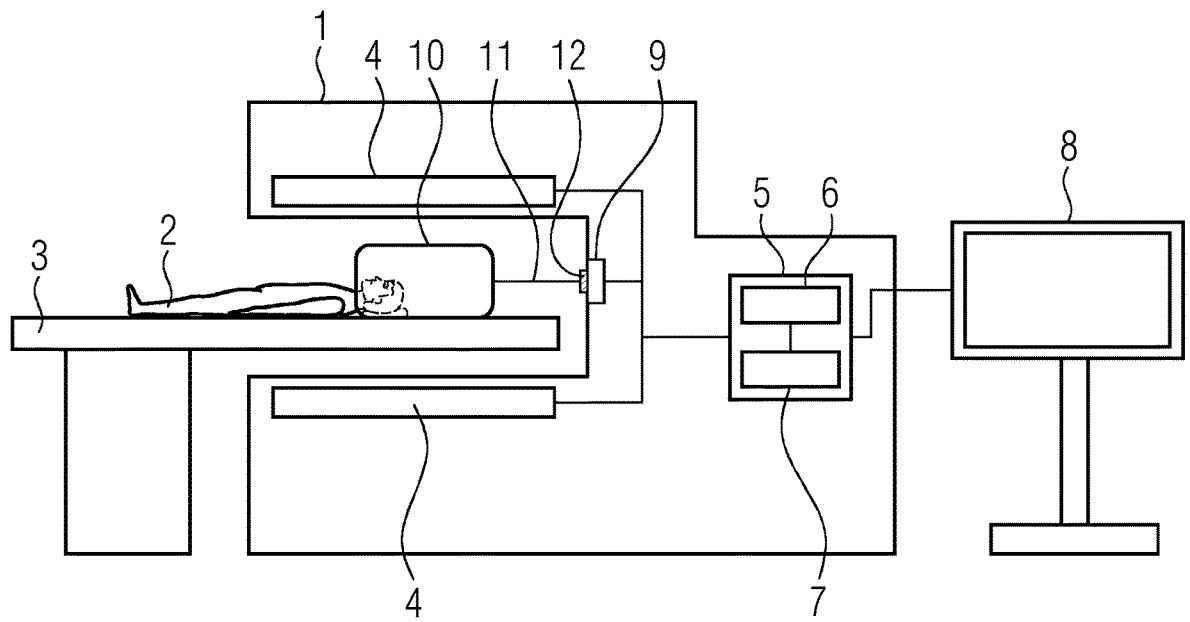

| Legend | | | | | |
|---|---|---|---|---|---|
| 1 | MR installation | 10 | coil facility | 19 | second receiver electronics module |
| 2 | patient | 11 | cable | 20 | central axis |
| 3 | patient couch | 12 | plug connector | 21 | examination space |
| 4 | magnet coils | 13 | housing | 22 | first actuator |
| 5 | control device | 14 | transmit resonator | 23 | second actuator |
| 6 | processor | 15 | transmitter electronics module | 24 | first telescopic rods |
| 7 | data memory | 16 | 1H receiver | 25 | second telescopic rod |
| 8 | display | 17 | first receiver electronics module | 26 | control module |
| 9 | interface | 18 | X-nucleus receiver | | |

FIG 2

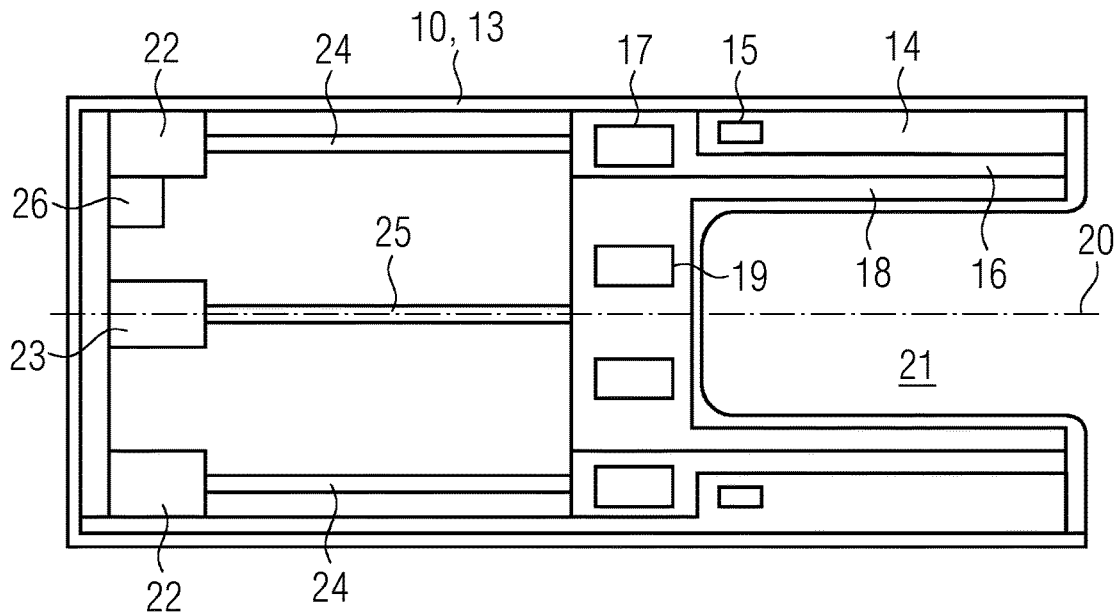

| Legend | |
|---|---|
| 13 | housing |
| 14 | transmit resonator |
| 15 | transmitter electronics module |
| 16 | 1H receiver |
| 17 | first receiver electronics module |
| 18 | X-nucleus receiver |
| 19 | second receiver electronics module |
| 20 | central axis |
| 21 | examination space |
| 22 | first actuator |
| 23 | second actuator |
| 24 | first telescopic rods |
| 25 | second telescopic rod |
| 26 | control module |

| Legend | | | |
|---|---|---|---|
| 13 | housing | 20 | central axis |
| 14 | transmit resonator | 21 | examination space |
| 15 | transmitter electronics module | 22 | first actuator |
| 16 | 1H receiver | 23 | second actuator |
| 17 | first receiver electronics module | 24 | first telescopic rods |
| 18 | X-nucleus receiver | 25 | second telescopic rod |
| 19 | second receiver electronics module | 26 | control module |

COIL FACILITY FOR A MAGNETIC RESONANCE INSTALLATION AND MAGNETIC RESONANCE INSTALLATION

This application claims the benefit of German Patent Application No. DE 10 2019 207 492.8, filed on May 22, 2019, which is hereby incorporated by reference in its entirety.

BACKGROUND

The present embodiments relate to a coil facility or coil arrangement for a magnetic resonance installation, and a corresponding magnetic resonance installation or a corresponding magnetic resonance system.

Magnetic resonance (MR) imaging today is an established technology for depicting examination objects (e.g., for medical applications). In this case, a magnetic field that penetrates the respective examination object is generated, atomic nuclei or magnetic moments are excited in the examination object, and resulting signals are captured by one or more receivers or receive coils, from which an image of the examination object may then be reconstructed in a known manner. Although functioning magnetic resonance installations have been available for some time, these installations are further developed in order to, for example, achieve a higher resolution or accuracy and ultimately a better image quality. A number of problems and challenges nonetheless arise in this case, such as increasingly noticeable interference effects and consequently a need for additional isolation and screening measures.

The resulting increase in demands and complexity provides that, for example, different coil facilities are to be used if the required imaging is based on the excitation of different types of atomic nuclei (e.g., in the case of relatively high magnetic field strengths and resolutions). For example, it is usually necessary initially to record a first measured data set using a first coil facility and excitation of the hydrogen nucleus or proton (e.g., 1H imaging). The coil facility is then to be changed, and a second measured data set is then to be recorded using a separate second coil facility (e.g., for excitation of an X-nucleus such as sodium nuclei). Such an exchange of the coil facility is resource-intensive and adversely affects a clinical workflow due to additional work stages and, for example, the problem that the respective examination object may move during the exchange of the coil facilities, thereby possibly having a negative influence on the final image quality.

Due to the cited requirements and complexity, it is, however, not currently possible simultaneously to position two high-channel receive arrangements for depictions based on different excitations in a hybrid antenna for generating two transmit modes at different frequencies, for example, without the occurrence of unacceptable interference effects. For example, the interference effects typically increase with the number of receive channels.

There is consequently further need for simplifications and improvements in the field of MR imaging using different excitation frequencies.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a structure that allows MR imaging to take place in a simplified manner and with greater efficiency in comparison with the prior art is provided.

An embodiment of a coil facility is provided for a magnetic resonance installation (e.g., for or for use in magnetic resonance (MR) imaging). The coil facility may therefore be connected to the respective magnetic resonance installation (e.g., attached to the respective MR installation via a cable or a plug connector). The coil facility may be mobile or portable, for example, and intended to depict only part of a patient (e.g., only a head or an arm and not for whole-body imaging). The coil facility may therefore have a maximum diameter of, for example, 50 cm and a maximum length of, for example, 1 m.

According to the present embodiments, the coil facility has a double-resonant transmit resonator for transmitting electromagnetic signals or fields of at least a first frequency and a second frequency differing therefrom into an examination space that is at least sectionally surrounded by the transmit resonator. The transmit resonator may also be operated as a receiver and therefore may also be referred to as a transmit/receive resonator. The transmit resonator may therefore be a radio-frequency or high-frequency transmit coil, by which the first frequency and the second frequency may be generated as two different transmit modes. For example, the first frequency and the second frequency may be resonance frequencies of the transmit resonator. Within the present embodiments, different frequencies may be frequencies that are identifiable as different (e.g., separate or discrete peaks in a spectrum or resonance curve) and not, for example, minimally varying frequencies of one and the same broad peak. For example, the first frequency may be provided for the 1H imaging, and the second frequency may be provided for the X-nucleus imaging. Accordingly, the first frequency may be, for example, 297 MHz and the second frequency may be, for example, 78 MHz for the excitation of protons or sodium nuclei using a $B_0$ magnetic field strength of 7 tesla in each case. The examination space may be that spatial region or volume in which the respective examination object is to be arranged during the imaging in order that MR images of the examination object may be recorded by or using the coil facility. The examination space may therefore correspond to a maximum depiction region or field of view (FoV).

The coil facility may have a first receiver for receiving signals corresponding to the first frequency and a second receiver for receiving signals corresponding to the second frequency. These corresponding signals or receive signals may lie in the first frequency or the second frequency in this case, but may be, for example, response or echo signals that are caused by excitation in the examination object as a result of the signal or field of the first frequency or the second frequency. The coil facility may therefore serve as a local coil. The first receiver and/or the second receiver may be or include one or a plurality of coils in each case, or a receive array including a plurality of individual receive elements.

The coil facility has an actuator system for effecting a relative spatial transposition of the transmit resonator, the first receiver, and the second receiver into various settings. The actuator system is therefore arranged and configured so as to transpose the transmit resonator and/or the first receiver and/or the second receiver relative to one or both of the other elements in each case. In a first setting or transposed position, only the first receiver is arranged in the examination space for the purpose of receiving the signals in this case. In a second setting or transposed position, only the second receiver is arranged in the examination space for the purpose of receiving the signals. The actuator system may include a plurality of individual actuators that may be activated, for example, independently of each other in this case.

The arrangement of one of the receivers in the examination space provides that this receiver is then arranged at least sectionally or largely within the transmit resonator (e.g., surrounded by the transmit resonator) and is therefore situated in the spatial volume that is penetrated or may be penetrated (e.g., in at least an essentially homogenous manner) by the electromagnetic signals that are generated by the transmit resonator. Conversely, an arrangement of one of the receivers outside the examination space provides that no significant coupling or signal transfer occurs between this receiver and the transmit resonator, and therefore, a field distribution within the examination space is not then influenced by this receiver or is only influenced to an extent that is negligible for the respective MR imaging. In other words, when operating the coil facility with the magnetic resonance installation, it is intended that no signals or fields for the MR imaging are measured by a receiver that is arranged outside the examination space.

For example, for a first operating mode of the coil facility, the first receiver may be arranged in a measurement setting for receiving the signals in the examination space, and the second receiver may simultaneously be arranged in a disengaged setting outside the examination space. For a second operating mode or operating state of the coil facility, it is conversely possible, using the actuator system, for the first receiver to be arranged in a disengaged setting outside the examination space and the second receiver to simultaneously be arranged in a measurement setting in the examination space.

For this purpose, the actuator system may be directly coupled or connected mechanically to the respective receiver in each case. However, the receivers may equally be secured on or to a respective carrier or carrier body or support structure. The actuator system may be mechanically connected or coupled to the carrier or carriers in order to transpose the carriers and therefore at least indirectly to likewise transpose the receiver or receivers secured thereto. The latter possibility may allow effective electrical or electromagnetic insulation of the receivers in this case (e.g., if the actuator system or a connection of the actuator system to the carrier or carriers is made entirely or partly from a metallic material).

The coil facility may also have further receivers that are then likewise secured in a manner that allows the further receivers to be transposed (e.g., individually) relative to the other receivers or the transmit resonator in the manner described, and which may be transposed by the actuator system.

The actuator system may include, for example, at least one electric motor or servomotor, a hydraulic system or pneumatic system, or other drive. The actuator system may likewise include, for example, a transmission, a threaded rod, a linear drive, a belt drive, a toothed-wheel or toothed-rack drive, and/or similar in order to allow particularly reliable transposition or transposability of the receivers or the transmit resonator. Ultimately, almost any known drive system from the field of mechanical engineering or drive technology may be deployed, at least to the extent that the drive system is MR-compatible or feasible. The components or parts of the actuator system or drive may therefore be, for example, non-magnetic, exhibit little or no electrical conductivity, be at least largely invisible for the purpose of MR imaging or for the antennas in use (e.g., in the case of 1H imaging and X-nucleus imaging), and not only interacting weakly with the electromagnetic fields of the antenna that are generated.

The coil facility may also include a control module or controller. This control module may be configured, for example, to control or trigger the actuator system and/or the transmit resonator and/or the receivers and/or a respective electronics module of the transmit resonator and/or the receivers.

By virtue of the mechanical displaceability of the receivers relative to each other or relative to the transmit resonator, particularly efficient operation of the transmit resonator and the respective receiver is possible in the described operating modes. Since the transposition by the actuator system is possible without movement of the coil facility as a whole (e.g., without movement of a housing of the coil facility in which the transmit resonator and the receivers are arranged), and without movement of the respective examination object, a clinical workflow and ultimately a resulting image quality may be improved by the present embodiments. This is the case because the change of the coil facility that was previously usual and necessary is no longer required.

In the case or operating mode where only the first receiver (e.g., configured for 1H imaging) is arranged in the examination space, for example, a reduction in transmit efficiency and field homogeneity that is comparatively relatively only slight in the context of an optimal signal-to-noise ratio for clinical applications may be produced, while parallel imaging and therefore an acceleration then become feasible. In the case or operating mode where only the second receiver (e.g., configured for X-nucleus imaging) is arranged in the examination space, this likewise produces a reduction in transmit efficiency and field homogeneity that is comparatively relatively only small in the context of likewise clinically desirable receive properties.

By contrast, the prior art makes no provision for the realization of a concurrent arrangement of two receivers (e.g., at least not two high-channel receivers) for different frequencies within the examination space or as part of a single compact coil facility, at least not in a manner that allows useful MR images.

Since the coil facility of the present embodiments may be integrated, configured, or realized as an individual compact unit (e.g., in a single housing), the present embodiments offer improved efficiency both with regard to workflow and use and with regard to electrical or electromagnetic factors and characteristics of the coil facility. In turn, it is ultimately possible thereby to reduce patient exposure and contribute to the success of an examination and/or treatment (e.g., by improving an image quality that may ultimately be achieved).

In an embodiment, the first receiver and the second receiver may simultaneously be transposed by the actuator system into a respective disengaged setting in which the first receiver and the second receiver are arranged outside the examination space. Provision is then made for the transmit resonator to be switchable into a receive mode in which the transmit resonator serves (e.g., in which the transmit resonator is used or may be used) as a receiver (e.g., for capturing or measuring signals in or from the examination space). In other words, provision is made for a third operating mode, in which only the transmit resonator, now effectively a transmit and receive resonator, is used to depict or measure the respective examination object, and no use is made of the two or more cited receivers that may be transposed relative to the transmit resonator. As a result of both or all of the transposable receivers therefore then being arranged outside the examination space and hence outside the transmit resonator, an optimal transmit and receive efficiency of the transmit resonator and an optimal field homogeneity are produced. This is desirable for optimal results and ultimately an optimal image quality in the case of quantitative measurements. It is thereby possible to achieve particularly good results, especially in the X-nucleus range, for example. The optimal image quality for quantitative measurement may be achieved if the transmit/receive profile is precisely known, and this is typically the case with single-channel birdcage coils. In this case, a lower signal-to-noise than may be achieved when using an RX array is accepted. The RX array has the disadvantage in principle that the RX array may cause inhomogeneities in the transmit field due to coupling effects and, when receiving, may have a footprint that is element-specific and patient-specific. In the case of conventional coil facilities or coil arrangements, a receive array is always arranged in the examination space, for example, and therefore always has a negative influence on the image quality and transmit efficiency. This may now be advantageously avoided.

In a further embodiment, the coil facility has a housing in which the transmit resonator, the receiver, and the actuator system are arranged. The transmit resonator is secured in a positionally fixed manner relative to the housing, either therein or thereon. This therefore provides that both or all receivers may be transposed, independently of each other, relative to the housing and relative to the transmit resonator by the actuator system. This embodiment allows a particularly compact and efficient structure of the coil facility, since the transmit resonator is used for all measurements and is therefore to surround, for example, a holder or support for the respective examination object at all times in measurement mode. As a result of the positionally fixed arrangement of the transmit resonator in the housing, this holder or support may then be configured in a particularly compact manner. A further advantage of a positionally fixed arrangement of at least one transmit element or receive element (e.g., the transmit resonator or one of the receivers) is that fixed electrical cabling or contacting, which does not move even if different settings or operating modes are selected, may then be installed for this element. This is advantageous and desirable, since it is thereby possible to avoid interfering effects and variability in the electrical functionality of the coil facility, which may be caused by, possibly inconsistent or non-reproducible, moving metallic or electrically conductive elements or parts of the coil facility. In addition to this, the actuator system may be configured so as to be more compact and lightweight and/or stable if the actuator system is only configured to reposition or transpose the receivers and not the transmit resonator.

In a further embodiment, the transmit resonator, the first receiver, and the second receiver, and further receivers if applicable, have a shape that is at least largely cylindrical or annular and are concentrically arranged around a common central axis extending through the examination space. The transmit resonator and the receivers may therefore be configured as cylinder coils or arranged on or along a circumferential surface of at least a notional cylinder. The central axis then corresponds to a central longitudinal axis of the cylinder. Such a concentric arrangement of the transmit and receive elements (e.g., of the transmit resonator and the receivers) allows a particularly compact structure of the coil facility at the same time as optimal field homogeneity and consistency of measurement results. For example, a coil facility diameter running transversely to the central axis thereof, or a space that is perpendicular to the central axis and is required for selecting the various settings or operating modes, may be kept particularly small in this way. This may be, for example, viewed in contrast with a structure of the coil facility in which the transmit or receive elements are arranged or secured so that the transmit or receive elements may be, for example, folded out laterally or swiveled out from the examination space. This provides that the coil facility may advantageously be deployed in patient holders of conventional tubular magnetic resonance tomographs, for example.

In a development, the receivers may be moved forwards and backwards independently of each other in an axial direction along the central axis relative to the transmit resonator by the actuator system in order to select the various settings or operating modes. In other words, the receivers may therefore travel or be moved in an axial direction out from the examination space or out from the transmit resonator and vice versa back in again. For this purpose, for example, different types of linear, worm, or creep drives, as described above, may be deployed as part of the actuator system. The embodiment of the coil facility provided here, including the axially repositionable receivers, allows a particularly compact structure of the coil facility, particularly in a diametrical or radial direction (e.g., in a transverse direction to the central axis). The actuator system may then be constructed in a particularly robust and reliable manner (e.g., because a complete circumference is available in each case as a point of application or contact between the actuator system or a connecting element driven by the actuator system and the receivers). Viewed in an axial direction along the central axis, the actuator system and, for example, a corresponding drive unit may then be advantageously arranged completely behind the examination space and therefore electrically insulated therefrom in a particularly simple and effective manner. It is thereby possible to avoid interference effects that may possibly otherwise influence respective measurement results or electrical functionality of the coil facility in an undesirable manner. A further advantage of the embodiment provided here (e.g., for research purposes or specific measurements) is that the receivers may be moved to intermediate settings in which the receivers are only partly arranged in the examination space, without thereby impeding or compromising an arrangement of an examination object or ability to arrange an examination object in the examination space.

In a development, the actuator system has telescopic elements or telescopic rods extending between a drive unit of the actuator system and the respective receiver in a manner that is at least essentially parallel or collinear with the central axis, for the purpose of moving the receivers. In this way, the telescopic elements may vary in length for the purpose of moving the receivers in an axial direction of the central axis. For example, the telescopic elements may include two or more elements. The two or more elements have at least essentially the shape of a tube or a rod and have different diameters that may be slid or inserted one inside the other (e.g., moved relative to each other). This likewise allows a particularly compact structure of the coil facility, since it is not necessary to provide, for example, additional housing space in order to accommodate connecting elements corresponding to the telescopic elements, but rigid and not of variable length, for all settings or operating modes. The telescopic elements provided here, or a corresponding telescopic drive, may, however, also be used for other geometries of the coil facility and/or arrangements of the transmit and/or receive elements.

In a further embodiment, the first receiver and/or the second receiver is configured as a receive array including a plurality of receive elements, each of which serves a receive channel. In one embodiment, at least 32 (e.g., 64 or 128 or more) individual receive elements may be provided per receive array. In this sense, the receive array provided here may therefore be referred to as a high-channel receive array. The individual receive elements may themselves take the form of individual coils or coil windings (RX loops), for example. The use of a receive array instead of an individual coil or a single-channel receiver may allow accelerated imaging by parallel measurements on the individual receive channels.

A particular advantage of the present embodiments is that both or all receivers may be configured as a multi-channel receive array, and MR measurement data or image data based on different excitations or on excitation frequencies may still be captured using just the one coil facility without image quality being adversely affected by the second receive array, in comparison with conventional coil facilities for an excitation frequency in each case.

The use of receive arrays is associated with additional challenges, since, for example, all individual attachment points and feed lines for the individual receive elements or receive channels are to be individually screened and, for example, equipped with sheath wave traps. The consequent complexity and a quantity of metallic or conductive material that is consequently required for the receiver provide that, as cited in this regard, the prior art does not allow simultaneous operation of two receive arrays for different excitation frequencies in the examination space (e.g., within the transmit resonator) for the purpose of imaging. The present embodiments solve this problem in a particularly simple manner and in this way simultaneously allows a particularly convenient and efficient use.

In a further embodiment, the coil facility has a respective electronics module for the first receiver and/or for the second receiver, and/or for one, a plurality, or all of the further receivers that may be provided. The electronics module or electronics modules include, in each case, an amplifier (e.g., a preamplifier) and/or an electrical or electronic logic circuit arrangement for switching or triggering elements or components of the respective receiver. Such elements or components, which may be switched or triggered by the logic circuit arrangement, may be, for example, PIN diodes or similar. The electronics module or electronics modules are arranged in this case on the respective receiver in a positionally fixed manner relative thereto, such that the respective electronics module follows the movement of the respective receiver when this is transposed. The electronics module of a receiver may be secured or fastened to the respective receiver in a separate housing and/or integrated into the receiver.

Such an embodiment including individual electronics modules and the arrangement thereof on the receivers or as part of the receivers has the advantage that the electronics module has a rigid electrical connection to the respective receiver or receive elements thereof, and may therefore be electrically attached via a fixed line or cabling that does not move, for example. This in turn provides that even if the respective receiver is transposed, there is no displacement or movement (e.g., unpredictable or inconsistent, non-reproducible) of the corresponding line or cabling relative to the receiver or relative to the transmit resonator. In comparison with a flexible mobile line or cabling, it is thereby possible to avoid interfering effects and variability that may adversely affect electrical characteristics of the coil facility as a whole.

This is also advantageous if the electronics module itself is electrically supplied via a flexible line, for example, since a single line may suffice to supply the electronics module, whereas individual elements of the respective receiver (e.g., individual diodes or receive elements or receive channels) are to be attached via respective individual lines in each case, which may result in a multiplication of the undesired adverse effects in comparison with the single attachment line of the electronics module. The attachment line for supplying the electronics module may be arranged further away from the examination space, whereby corresponding interference effects may be further reduced.

The electronics module in the sense described here may be configured to control, switch, and/or electrically supply the respective receiver or individual parts or elements thereof. Accordingly, the electronics module may include different sub-circuits, electrical and/or electronic parts, and the like.

In a further embodiment, the coil facility has a control device (e.g., a control module, control circuit, or controller) and respective adjustment circuits or adjustment circuit arrangements that may be triggered thereby for the purpose of frequency adjustment or tuning of the receivers and/or the transmit resonator. The control device in this case is configured to automatically activate or deactivate the adjustment circuits as a function of the respective setting of the receiver relative to the transmit resonator (e.g., as a function of the currently selected operating mode of the coil facility). The control device may control the actuator system directly in this case or be connected to the actuator system or a control module of the actuator system and/or to a sensor system for capturing a current setting of the receivers or the transmit resonator in order to capture corresponding setting data that specifies the current setting of the transmit and receive elements, or thereby to provide setting data.

The adjustment circuits are activated and deactivated by the control device in the specified manner as a function of the setting of the receivers. For this purpose, for example, corresponding switching specifications may be stored in a data memory or as part of an operating program of the control device. The adjustment circuits, also referred to as tuning or match circuits, are configured and specified to set predefined characteristics or a predefined functionality of the respective transmit or receive element (e.g., of the transmit resonator or of the respective receiver) in a predetermined manner (e.g., to perform or bring about a frequency adjustment or tuning or similar). It is thereby possible in each case to achieve an optimal efficiency and accuracy of the coil facility overall in all of the various settings or operating modes.

The adjustment circuits may be part of the electronics module or electronics modules cited elsewhere, for example. Accordingly, for example, the adjustment circuits of the receivers may be arranged on or integrated into the receivers (e.g., arranged in a positionally fixed manner relative thereto even during transposition of the respective receiver), such that the adjustment circuits follow the movement of the respective receiver when this is transposed. Likewise, it is then possible to avoid mobile cabling or electrical contacting between the adjustment circuits and the respective receiver in order to avoid or reduce corresponding interfering effects or variabilities in the electrical functionality of the coil facility.

The adjustment circuits may be constructed in each case from one or more capacitors and/or resistors and/or similar, and effect an adjustment or tuning to a respective load in a manner that is known from the field of electronics engineering. This may be particularly advantageous in the case of high magnetic field strengths (e.g., in the case of 7 T provided for research purposes and possibly for future applications) in order to achieve sufficient efficiency of the coil facility and ultimately a particularly good image quality.

It is due to the mobility of the receivers that the adjustment circuits may be particularly useful here, based on the finding that resonance frequencies or resonance peaks of the transmit or receive elements may shift by up to 3 MHz, for example, as a function of the respective setting of the receivers relative to the transmit resonator. This may be caused or influenced, for example, by the fact that, in a measurement setting of a receiver (e.g., when this is situated in the examination space), eddy currents may form on a surface of the receiver, where the eddy currents may influence a field distribution in the examination space or a coupling between the transmit resonator and the respective receiver. These effects disappear when the receiver is repositioned to the disengaged setting (e.g., is no longer situated in the examination space). The adjustment circuits provided here therefore represent a further development of the coil facility of the present embodiments based on the specific properties and requirements thereof.

A further aspect of the present embodiments is a magnetic resonance installation (e.g., MR installation or MRT) that includes a coil facility according to the present embodiments and a control module for triggering the coil facility and for capturing measurement signals supplied by the coil facility. For example, the magnetic resonance installation according to the present embodiments may be the magnetic resonance installation cited in connection with the coil facility of the present embodiments. Accordingly, the magnetic resonance installation of the present embodiments may have the properties or features cited or described in connection with the coil facility of the present embodiments. The coil facility may be connected to a main part of the magnetic resonance installation via a cable, an attachment point, or an interface, for example. In an embodiment, this connection may be reversibly separable, thereby allowing the coil facility to be connected to the rest of the magnetic resonance installation only when required (e.g., in a particularly flexible manner).

In this case, the magnetic resonance installation may as usual have a control module, an electronics module, a power supply, and an operator or user interface for operation without the coil facility. These components may then also be used during operation of the magnetic resonance installation when using the coil facility, and therefore need not be redundantly arranged in the coil facility itself. The control module of the magnetic resonance installation is arranged outside the coil facility in this case (e.g., outside a housing of the coil facility), whereby electromagnetic interference of the coil facility or of the measurement signals supplied or captured by the coil facility may be avoided or reduced.

The control module of the magnetic resonance installation may control a power supply of the coil facility, for example, and send control signals or instructions to the coil facility in order to deploy or select a setting of the transmit and receive elements (e.g., an operating mode of the coil facility). It is therefore not necessary, in the context of a specific planned measurement or examination, for a respective user to select the setting of the transmit and receive elements of the coil facility at the coil facility itself; this thereby allows a workflow that is simpler and, for example, more efficient when using the coil facility.

The properties and developments of the coil facility of the present embodiments and of the magnetic resonance installation of the present embodiments, as well as corresponding advantages, as specified above and below, are reciprocally interchangeable and transferable in each case between these aspects of the present embodiments. The present embodiments therefore also encompass developments of the coil facility and the magnetic resonance installation including embodiments that, in order to avoid unnecessary redundancy, are not explicitly described in the respective combination or for each aspect of the present embodiments separately.

BRIEF DESCRIPTION OF THE DRAWINGS

FIG. 1 shows a schematic side view of one embodiment of a magnetic resonance installation with a local coil facility attached thereto;

FIG. 2 shows a schematic cross-sectional side view of one embodiment of the coil facility;

DETAILED DESCRIPTION

Figure 3:
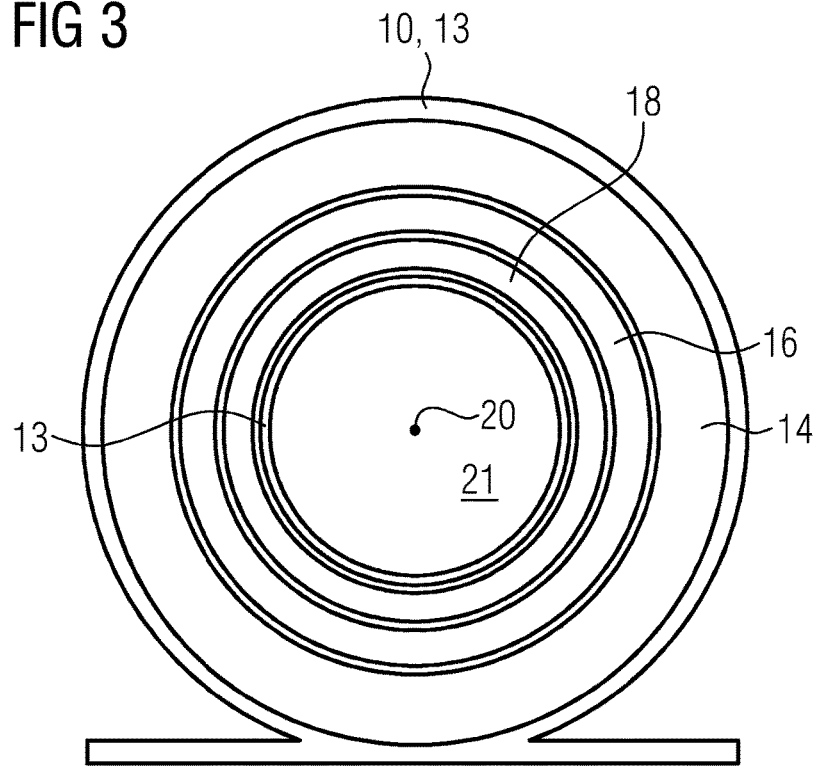
FIG. 3 shows a schematic cross-sectional front view of one embodiment of the coil facility.

In the exemplary embodiments, components described in relation to the variants represent in each case individual features that are to be considered independent of each other, and also in each case develop the invention independently of each other and therefore are to be considered as part of the invention individually or in a combination other than that shown. The variants described below may also be supplemented by further features of the invention already described above.

Those elements in the figures that are the same, functionally same, or correspond to each other are identified by the same reference signs in each case.

In the field of magnetic resonance imaging, multi-core high-frequency transmit coils may be constructed from two transmit and receive structures nested within each other. The objective of maximum efficiency for $B_1$ field generation and maximum homogeneity in a defined spatial volume may conventionally be achieved, for example, through the use of a birdcage (BC) structure. Known TEM structures may likewise be used as an alternative. A BC structure is typically constructed from two end rings that are connected together by a number of rods that are disposed perpendicularly to the annular areas thereof (e.g., longitudinally). A resonance frequency that is desired in each case may be selected by capacitors in the rods (e.g., low-pass BC) or in the end rings (e.g., hi-pass BC), for example. By suitable feed-in points (e.g., four feed-in points having in each case a 90° angle offset in a circumferential direction) and a suitable phase offset, a sinusoidal or cosinusoidal current density distribution is obtained in a circumferential direction. This produces a circularly polarized homogeneous high-frequency field in the center of the respective coil (e.g., the respective BC structure) for example. The high-frequency field is to be generated in this case for different types of imaging, based on the excitation of different types of atomic nuclei, with correspondingly different frequencies. This may be achieved conventionally by two electrically isolated antenna structures, for example, or a hybrid antenna may be used whereby, for example, for the purpose of 1H imaging and X-nucleus imaging, two transmit modes corresponding to the required frequencies are produced on a shared electrical structure.

It is, however, important to prevent parasitic coupling between the antenna structures in this case. Suitable isolation measures may be deployed for this purpose (e.g., active and passive resonant rejection circuits in the rods and end rings of the BC structures). Without these measures, the field homogeneity and transmit efficiency of the transmit coil would be significantly worse, and a resulting image quality would ultimately also suffer from this. This issue is particularly relevant in the case of short wavelengths relative to the size or extent of a respective examination object, such as those occurring at frequencies of, for example, 297 MHz for 1H imaging using 7 tesla, or at even higher frequencies.

In a hybrid antenna (e.g., a double-resonant transmit coil), a receive array, for example, may be operated for the X-nucleus imaging. Introducing such a receive array (RX array) into the transmit coil may, however, disadvantageously result in field inhomogeneities, reduce a transmit efficiency (TX efficiency) of the transmit coil, and potentially have a negative effect on a signal-to-noise ratio of the receive array. Even if at comparatively significant technical expense, a compromise may be found for integrating a corresponding receive array into the transmit coil, taking these disadvantages and the associated technical complexity into account, it is not realistically possible according to the available prior art to also integrate a second receive array into the transmit coil for a further imaging modality or excitation frequency. It is, however, precisely this that would be desirable (e.g., in clinical operation) in order to avoid a resource-intensive coil change during the examination as previously required, when, for example, a coil having a receive array for 1H imaging is exchanged for a coil having a receive array for X-nucleus imaging (e.g., based on the excitation of $^{23}$Na nuclei).

For example, a magnetic resonance installation as illustrated in a schematic side view in FIG. 1 and referred to simply as MR installation 1 may be used to resolve this problem. The MR installation 1 is primarily used to examine (e.g., depict) a patient 2 who is shown lying on a patient couch 3. The MR installation 1 has an arrangement of magnet coils 4, only indicated schematically here, and a control device 5 that is connected to the magnet coils 4 for the triggering thereof. The control device 5 includes, for example, at least one processor 6 and a data memory 7 that is connected thereto. For example, an operating program for operating the MR installation 1 may be stored in the data memory 7, where the operating program may be executed by the processor 6 for the purpose of operating (e.g., controlling) the MR installation 1. The MR installation 1 may also have further components or parts that are known from conventional magnetic resonance installations but are not illustrated in FIG. 1 for the sake of clarity. Also illustrated in FIG. 1 is a display 8 that is connected to the control device 5. For example, MR images generated by the control device 5 or another facility of the MR installation 1 may be displayed by the display 8.

The MR installation 1 also has an interface 9 that is likewise connected to the control device 5. The interface 9 is, for example, likewise shown schematically and may be used, for example, to transfer both electrical power and measurement or data signals as well as control signals. Accordingly, the interface 9 may include a plurality of individual attachment points or connections, for example.

In order to depict, for example, a head of the patient 2, provision is made for a mobile local coil facility 10 that is connected to a main part or main body of the MR installation 1 by a cable 11 with a plug connector 12 via the interface 9. The coil facility 10 is, for example, mobile or transportable and may therefore be attached via the interface 9 only when required. Like the magnet coils 4, the coil facility 10 may then be triggered by the control device 5 and supplied with electrical power via corresponding entities of the MR installation 1. For example, high-frequency pulses on the coil facility 10 may be specified by the control device 5 in accordance with a measuring sequence that is predetermined or selected by a respective user, and resulting response signals or measurement signals that are captured by the coil facility 10 may be recorded and evaluated (e.g., processed to produce an MR image). Different operating modes or operating settings of the coil facility 10, which are explained in further detail below, may likewise be specified or selected by the control device 5.

FIG. 2 shows a schematic cross-sectional side view of the coil facility 10. The coil facility 10 has, for example, a housing 13. Arranged in the housing 13 are a transmit resonator 14 with a transmitter electronics module 15 arranged thereon or integrated therein, a 1H receiver 16 for proton imaging with a first receiver electronics module 17 arranged thereon or integrated therein, and an X-nucleus receiver 18 with a second receiver electronics module 19 arranged thereon or integrated therein. The transmit resonator 14, the 1H receiver 16, and the X-nucleus receiver 18 are also referred to jointly as transmit and receive elements 14, 16, 18. The transmit and receive elements 14, 16, 18 are, for example, configured so as to be essentially cylindrical and are arranged concentrically in relation to each other around a shared central axis 20. The transmit and receive elements 14, 16, 18 therefore surround an examination space 21 in which, for example, the head of the patient 2 to be depicted may be supported. In an exemplary realization of the coil facility 10, the examination space 21 may have, for example, a length or extent of approximately 30 cm in the direction of the central axis 20. The coil facility 10 may therefore be significantly smaller than conventional magnetic resonance installations and may therefore be deployed and arranged in a particularly flexible manner.

The transmit resonator 14 takes, for example, the form of a double-resonant transmit and receive coil or antenna for the 1H and X-nucleus imaging. The 1H receiver 16 is configured as a multi-channel receive array for the proton imaging and the X-nucleus receiver 18 likewise as a multi-channel receive array for the X-nucleus imaging. The receivers 16, 18 in this case may each have at least 32 (e.g., up to 128 or more) individual receive channels (e.g., corresponding receiver or RX loops). All these individual channels or RX loops are, for example, isolated from each other, at least within corresponding receive bandwidth, and are additionally protected by corresponding screening or isolation against interference by the transmit resonator 14 at other frequencies. In addition, corresponding feed lines or attachment lines for each channel are equipped with individual sheath wave traps against interference. By these measures, it is possible to prevent inhomogeneities in the transmit fields generated by the transmit resonator 14 for the 1H and X-nucleus imaging, and therefore, for example, an undesired focusing of HF power by the RX loops and feed lines. In the configuration schematically illustrated in FIG. 2, in which both the 1H receiver 16 and the X-nucleus receiver 18 are moved into their respective measurement settings in the transmit resonator 14 or examination space 21, it is impossible, as described above, to perform any meaningful imaging according to existing knowledge, since the total amount of material and components then disposed within the transmit resonator 14 results in excessive impairment.

In order to resolve this problem, the receivers 16, 18, including corresponding electronics modules 17, 19, may be mechanically transposed relative to the transmit resonator 14 and the examination space 21 into a respective disengaged setting, in which the receivers 16, 18 are arranged outside the transmit resonator 14 and the examination space 21. The receivers 16, 18 may be transposed independently of each other in this case, so that in corresponding different operating modes of the coil facility 10, neither of the two receivers 16, 18 or only the 1H receiver 16 or only the X-nucleus receiver 18 is arranged or may be arranged in the respective measurement setting (e.g., within the transmit resonator 14).

A first actuator 22 is provided for the purpose of transposing (e.g., moving the 1H receiver 16 in an axial direction along the central axis 20). A separate, second actuator 23 is provided for the purpose of axially transposing the X-nucleus receiver 18. The actuators 22, 23 are likewise accommodated within the housing 13 in this case. The actuator 22 is, for example, connected to the 1H receiver 16 or a carrier body, on which the 1H receiver 16 is secured, via a plurality of first telescopic rods 24 that are uniformly distributed over a circumference of the 1H receiver 16. The second actuator 23 is, for example, mechanically coupled to the X-nucleus receiver 18 or the carrier body thereof by a second telescopic rod 25. For example, the second telescopic rod 25 extends along the central axis 20 in this case, while the first telescopic rods 24 are arranged further out radially and parallel thereto. Therefore, the receivers 16, 18 may be moved independently of each other and also simultaneously or in opposite directions, for example.

The actuators 22, 23 may be controlled by a control module 26 of the coil facility 10 in this case. The control module 26 is likewise arranged within the housing 13 and may be used (e.g., configured) to communicate with the MR installation 1 and/or the control device 5 thereof. The control module 26 may equally be used (e.g., configured) to control or switch the electronics modules 15, 17, 19. For this purpose, the control module 26, like the control device 5, may include, for example, a processor facility and a memory facility and/or a hardware circuit arrangement or similar.

For example, a specific operating mode (e.g., a use of a specific partial coil system of the coil facility 10) may be selected by a respective user via a user interface of the MR installation 1 or of the control device 5. The control device 5 then sends a corresponding instruction or requirement to the coil facility 10 via the cable 11. This instruction or requirement may then be received and processed by the control module 26 of the coil facility 10, and converted into a corresponding control signal for the actuators 22, 23 and, if applicable, for the electronics modules 15, 17, 19. For example, depending on the selected operating mode (e.g., according to the setting of the receivers 16, 18), the control module 26 may activate or deactivate a respective adjustment circuit 29 (see FIG. 7). For the purpose of sending corresponding control signals and likewise returning measurement signals recorded by the receivers 16, 18 to the control module 26 or to the control device 5, an electrical cabling or contacting of the receivers 16, 18 may be guided through or along the telescopic rods 24, 25, for example. Guidance of the cabling within the telescopic rods 24 or 25 may have the advantage that the telescopic rods 24, 25, in addition to the regular function of moving the receivers 16, 28, may also function as electromagnetic screening for the respective cabling. The telescopic rods 24, 25 may also restrict a movement of the cabling when the receivers 16, 18 are repositioned or transposed, so that any interference effects resulting therefrom may be reduced accordingly. The transmit resonator 14 may be attached via cabling or a line that is stationary (e.g., positionally fixed). For this purpose, a tail or attachment region of the transmit resonator 14, as illustrated by way of example, may extend possibly as far as that end of the coil facility 10 that is opposite the examination space 21.

FIG. 3 shows a schematic cross-sectional front view of the coil facility 10 looking along the central axis 20. The cylindrical or annular embodiment and the concentric arrangement of the transmit and/or receive entities 14, 16, 18 around the examination space 21 and the central axis 20 is shown. In an exemplary realization of the coil facility 10, a free diameter of the examination space 21 for accommodating the respective examination object (e.g., part of the patient 2 in this case) may have a diameter of approximately 20 cm, for example. The X-nucleus receiver 18 adjacent to this in a radial direction outwards may have a wall thickness of 1.5 cm, for example, and therefore an overall diameter of approximately 23 cm. The 1H receiver 16 arranged outside this in a radial direction may likewise have a wall thickness of 1.5 cm, for example, and therefore an overall diameter of approximately 26 cm. The transmit resonator 14 arranged outside the 1H receiver 16 in a radial direction may have a wall thickness of 3 cm, for example, and therefore an overall diameter of approximately 32 cm. Since the housing 13 is then situated radially outside the transmit resonator 14, the whole coil facility 10 in this exemplary realization may therefore have a diameter of approximately 36 cm, for example. The dimensions specified serve, for example, merely as an example for a possible realization. Therefore, the coil facility 10 may equally be realized in other dimensions, sizes, size ratios, and/or shapes.

Figure 4:
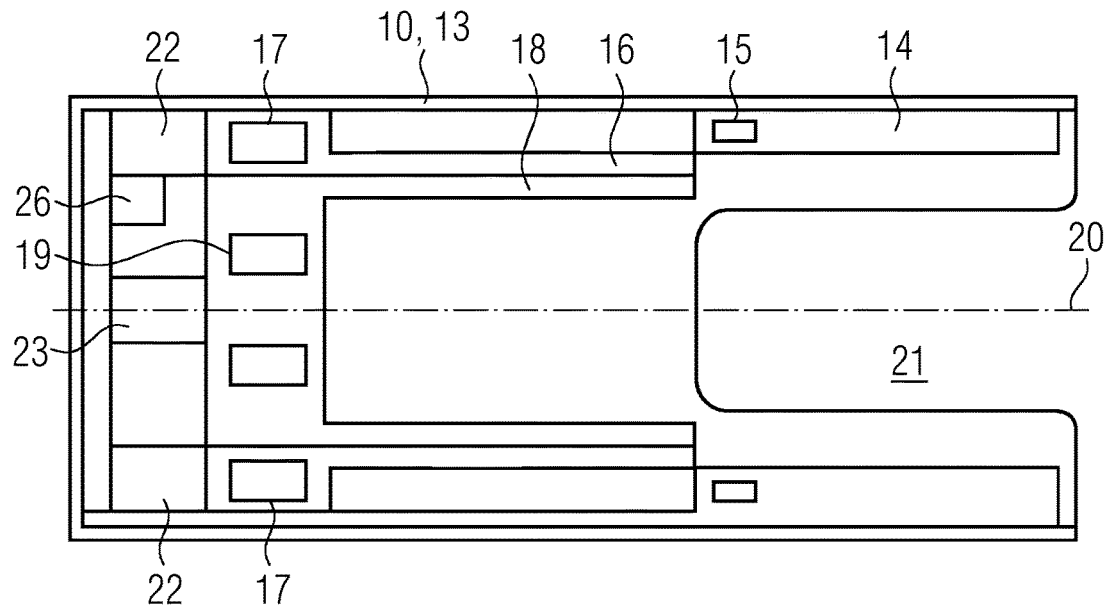
FIG. 4 shows a schematic cross-sectional side view of one embodiment of the coil facility in a first operating mode.

FIG. 4 shows a schematic cross-sectional side view of the coil facility 10 in a first operating mode. In the first operating mode, both receivers 16, 18 are arranged in a respective disengaged setting (e.g., outside the transmit resonator 14). The telescopic rods 24, 25 are retracted to minimal lengths by the actuators 22, 23, respectively. In this setting, the telescopic rods 24, 25 may be accommodated in, for example, corresponding locating spaces or recesses in the schematically indicated actuators 22, 23 or housings thereof. Since no receive arrays are situated in the field of view (FoV) or recording region of the coil facility 10 in the first operating mode, an optimal transmit and receive efficiency of the transmit resonator 14 and an optimal field homogeneity are produced. This provides that, for example, particularly accurate quantitative measurements may be conducted in the context of proton imaging.

Figure 5:
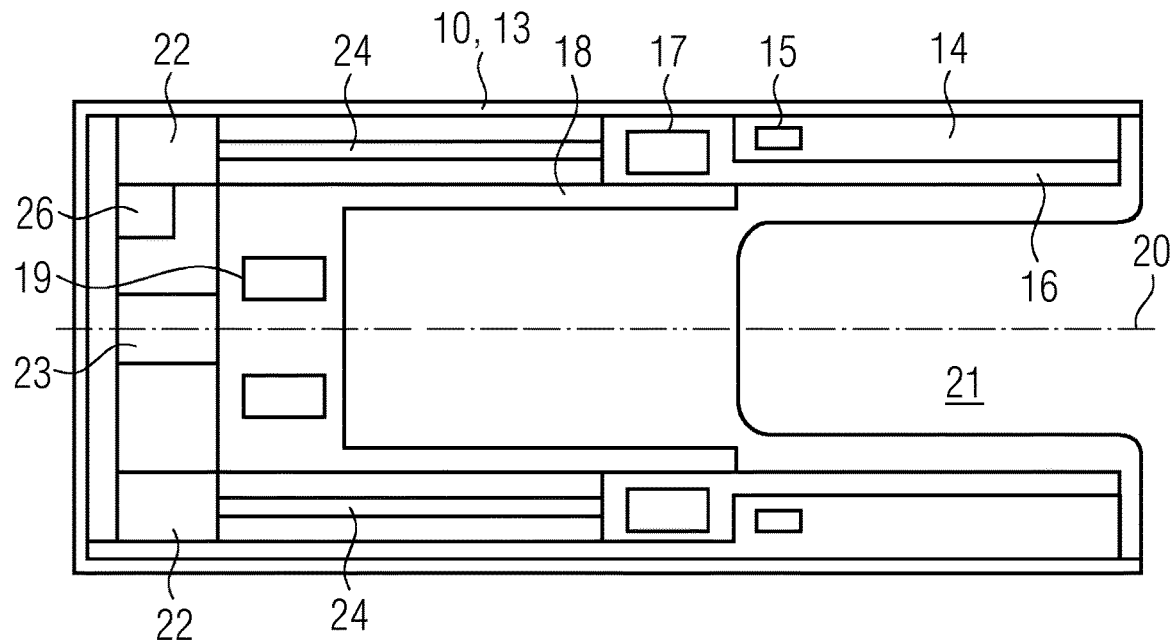
FIG. 5 shows a schematic cross-sectional side view of one embodiment of the coil facility in a second operating mode.

FIG. 5 shows a schematic cross-sectional side view of the coil facility 10 in a second operating mode. In the second operating mode, the X-nucleus receiver 18 is still in a disengaged setting, while the 1H receiver 16 has been transposed into a measurement setting in the transmit resonator 14. In this case, the first telescopic rods 24 are extended to a maximal length by the first actuator 22. Since in this operating mode, instead of the transmit resonator 14, the 1H receiver 16 that is configured as a multi-channel receive array is for example, then used to capture the measurement signals for the proton imaging, it is possible to apply an acceleration factor of >1 (e.g., parallel imaging). It is advantageous in this case that neither the efficiency of the relevant transmit and receive elements 14, 16 nor image quality is adversely affected by the X-nucleus receiver 18, since this is situated in a disengaged setting far enough outside the examination space 21 for interfering effects to be at least largely avoided.

Figure 6:
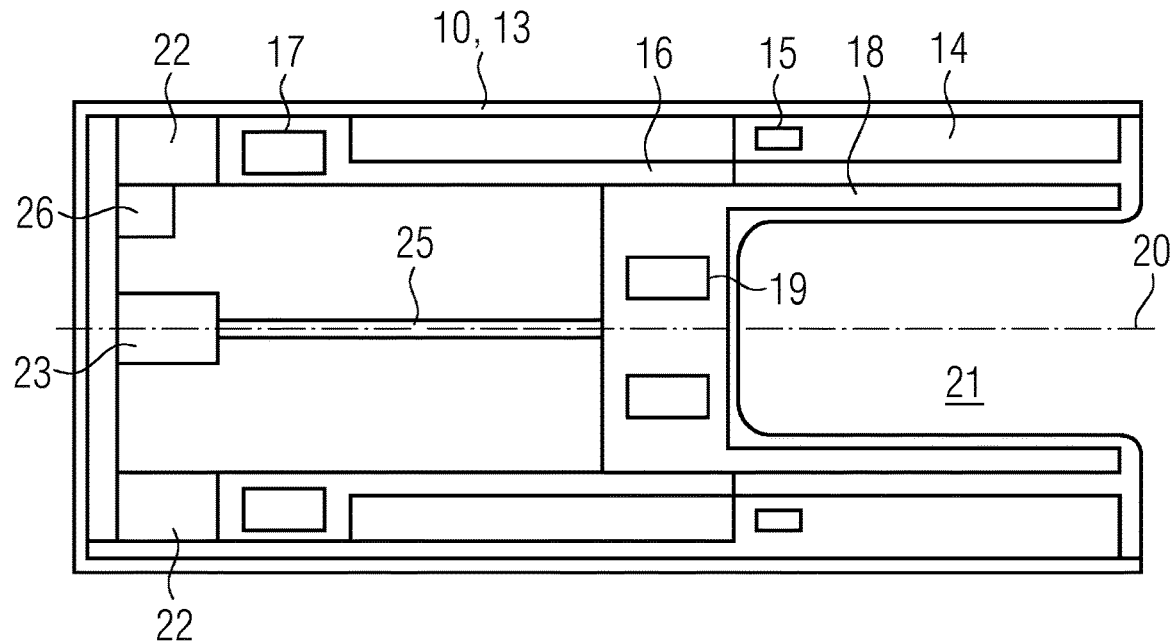
FIG. 6 shows a schematic cross-sectional side view of one embodiment of the coil facility in a third operating mode.

FIG. 6 shows a schematic cross-sectional side view of the coil facility 10 in a third operating mode. In this case, only the X-nucleus receiver 18 for the purpose of X-nucleus imaging is arranged in the measurement setting in the transmit resonator 14 (e.g., in or surrounding the examination space 21), while the 1H receiver 16 is arranged in the disengaged setting. Therefore, the second telescopic rod 25 is extended to the maximal length in this case, while the first telescopic rods 24 are retracted to the minimal length or compressed. It is therefore possible to undertake measurements by a multi-channel receive array in the form of the X-nucleus receiver 18 without the second receive array in the form of the 1H receiver 16, which is then not required, interfering with the measurement.

Figure 7:
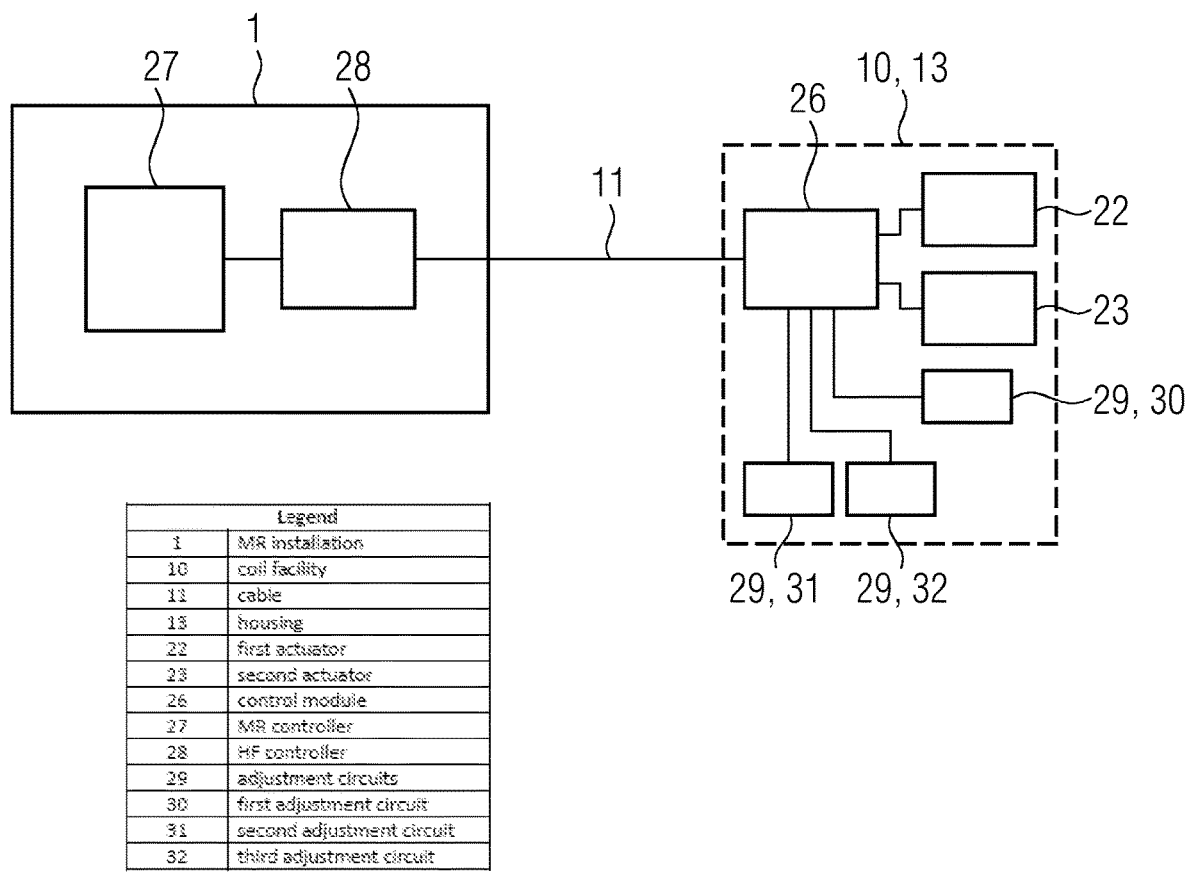
FIG. 7 shows a schematic overview of one embodiment of a circuit arrangement for the magnetic resonance installation and the coil facility.

FIG. 7 shows a schematic overview to illustrate a logical interconnection of the components described above. The MR installation 1 has, for example, an MR controller 27 and an HF controller 28 that is monitored or triggered thereby. The controllers 27, 28 may be part of the control device 5, for example, or separate entities of the MR installation 1. Using the MR controller 27, it is possible to control or manage a selection of a sequence to be used and an operating mode of the coil facility 10 that is required for this purpose. The HF controller 28 may then control the generation of corresponding HF pulses and the like. Signals sent by the controllers 27, 28 via the cable 11 to the coil facility 10 may be received and processed there, for example, by the control module 26, as described above. For example, the control module 26 may control the previously mentioned adjustment circuits 29 in addition to the actuators 22, 23. In this case, a first adjustment circuit 30, a second adjustment circuit 31, and a third adjustment circuit 32 are provided. For example, each of the adjustment circuits 29 may be assigned to one of the described three operating modes of the coil facility 10 or to one of the transmit and receive elements 14, 16, 18. Depending on the operating mode selected or used by the coil facility 10, or on which of the transmit and receive elements 14, 16, 18 is or are used for a respective measurement, the relevant assigned adjustment circuit 29 or adjustment circuits 29 may be automatically activated by the control module 26 and the correspondingly unused adjustment circuits 29 automatically deactivated.

In summary, provision is made for a coil body in the form of the coil facility 10. The coil body includes two receive coils that may be mechanically displaced in opposite directions. Alternatively, provision is made for two carrier bodies that may be mechanically displaced in opposite directions for the receive coils, described here in the form of the receivers 16, 18. Using the geometry provided here, a radially inner carrier body may accommodate the RX loops of the X-nucleus receiver 18, as well as the feed lines and electronics module 19 thereof, including, for example, a preamplifier and/or mixer. A radially outer carrier body may be constructed and arranged concentrically relative thereto, and may accommodate the corresponding parts or components of the 1H receiver 16. The two carrier bodies are then secured or supported such that an axial displacement of the two carrier bodies, and therefore also the two receivers 16, 18, relative to each other is possible. This support and displacement or displaceability is configured such that in a respective extended or retracted state, in which the respective receiver 16, 18 is outside the FoV of the coil facility 10 or of the transmit resonator 14, no significant coupling of the respective receiver 16, 18 with the transmit resonator 14 occurs. This provides that operation is possible with optimal efficiency. For example, the advantage is obtained that a second, separate coil and corresponding coil change is no longer required for the X-nucleus imaging in addition to the proton imaging in clinical applications. Therefore, both clinical proton imaging and X-nucleus imaging are possible without changing the coil facility 10. By virtue of only the required receiver 16, 18 being moved to the measurement setting in each case, provision is made in each case for an optimal transmit efficiency and field homogeneity and/or an optimized signal-to-noise ratio and the possibility of applying acceleration factors >1 for parallel imaging in combination with a double-resonant HF transmit coil, provided here in the form of the transmit resonator 14.

Together, the examples described above show how a structure that may make it possible for MR imaging to take place in a simplified manner and with greater efficiency in comparison with the prior art may be realized.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A coil facility for a magnetic resonance installation, the coil facility comprising:
    a double-resonant transmit resonator operable to transmit electromagnetic signals of a first frequency and a second frequency into an examination space, the second frequency differing from the first frequency, the examination space being surrounded at least sectionally by the double-resonant transmit resonator;
    a first receiver operable to receive signals corresponding to the first frequency;
    a second receiver operable to receive signals corresponding to the second frequency; and
    an actuator system operable for effecting a spatial transposition of the first receiver and the second receiver, independently of each other, relative to the double-resonant transmit resonator into various settings, such that in a first setting, only the first receiver is arranged in the examination space, and in a second setting, only the second receiver is arranged in the examination space for the purpose of receiving the signals.

2. The coil facility of claim 1, wherein the first receiver and the second receiver are simultaneously transposable by the actuator system into a respective disengaged setting in which the first receiver and the second receiver are arranged outside the examination space, and
wherein the double-resonant transmit resonator is switchable into a receive mode.

3. The coil facility of claim 1, further comprising a housing in which the double-resonant transmit resonator, the first receiver, the second receiver, and the actuator system are arranged,
wherein the double-resonant transmit resonator is secured in a positionally fixed manner relative to the housing.

4. The coil facility of claim 1, wherein the double-resonant transmit resonator, the first receiver, and the second receiver have a shape that is at least largely cylindrical and are concentrically arranged around a common central axis extending through the examination space.

5. The coil facility of claim 4, wherein the first receiver and the second receiver are movable forwards and backwards independently of each other in an axial direction along the central axis relative to the double-resonant transmit resonator by the actuator system in order to select the various settings.

6. The coil facility of claim 4, wherein the actuator system includes telescopic elements that extend at least essentially parallel with the central axis between a drive unit of the actuator system and the respective receiver of the first receiver and the second receiver for the purpose of moving the first receiver and the second receiver, and
wherein the telescopic elements are variable in length for the purpose of moving the first receiver and the second receiver in an axial direction of the central axis.

7. The coil facility of claim 1, wherein the first receiver, the second receiver, or the first receiver and the second receiver are each configured as a receive array comprising a plurality of receive elements, each receive element of the plurality of receive elements serving as a receive channel.

8. The coil facility of claim 7, wherein the plurality of receive elements include at least 32 receive elements.

9. The coil facility of claim 1, further comprising a respective electronics module for the first receiver, the second receiver, or the first receiver and the second receiver, the respective electronics module comprising an amplifier, a logic circuit arrangement, or the amplifier and the logic circuit arrangement for switching or triggering elements of the respective receiver of the first receiver and the second receiver and being arranged on the respective receiver of the first receiver and the second receiver in a positionally fixed manner relative thereto, such that the respective electronics module follows a movement of the respective receiver of the first receiver and the second receiver when this is transposed.

10. The coil facility of claim 1, further comprising a controller and respective adjustment circuits that are triggerable thereby for frequency adjustment of the first receiver and the second receiver, the double-resonant transmit resonator, or the first receiver, the second receiver, and the double-resonant transmit resonator, and
wherein the controller is configured to activate or deactivate the adjustment circuits as a function of the respective setting of the first receiver and the second receiver relative to the double-resonant transmit resonator.

11. A magnetic resonance installation comprising:
a coil facility comprising:
a double-resonant transmit resonator operable to transmit electromagnetic signals of a first frequency and a second frequency into an examination space, the second frequency differing from the first frequency, the examination space being surrounded at least sectionally by the double-resonant transmit resonator;
a first receiver operable to receive signals corresponding to the first frequency;
a second receiver operable to receive signals corresponding to the second frequency; and
an actuator system operable for effecting a spatial transposition of the first receiver and the second receiver, independently of each other, relative to the double-resonant transmit resonator into various settings, such that in a first setting, only the first receiver is arranged in the examination space, and in a second setting, only the second receiver is arranged in the examination space for the purpose of receiving the signals; and
a controller configured to:
trigger the coil facility; and
capture measurement signals supplied by the coil facility.

12. The magnetic resonance installation of claim 11, wherein the first receiver and the second receiver are simultaneously transposable by the actuator system into a respective disengaged setting in which the first receiver and the second receiver are arranged outside the examination space, and
wherein the double-resonant transmit resonator is switchable into a receive mode.

13. The magnetic resonance installation of claim 11, wherein the coil facility further comprises a housing in which the double-resonant transmit resonator, the first receiver, the second receiver, and the actuator system are arranged, and
wherein the double-resonant transmit resonator is secured in a positionally fixed manner relative to the housing.

14. The magnetic resonance installation of claim 11, wherein the double-resonant transmit resonator, the first receiver, and the second receiver have a shape that is at least largely cylindrical and are concentrically arranged around a common central axis extending through the examination space.

15. The magnetic resonance installation of claim 14, wherein the first receiver and the second receiver are movable forwards and backwards independently of each other in an axial direction along the central axis relative to the double-resonant transmit resonator by the actuator system in order to select the various settings.

16. The magnetic resonance installation of claim 14, wherein the actuator system includes telescopic elements that extend at least essentially parallel with the central axis between a drive unit of the actuator system and the respective receiver of the first receiver and the second receiver for the purpose of moving the first receiver and the second receiver, and
wherein the telescopic elements are variable in length for the purpose of moving the first receiver and the second receiver in an axial direction of the central axis.

17. The magnetic resonance installation of claim 11, wherein the first receiver, the second receiver, or the first receiver and the second receiver are each configured as a receive array comprising a plurality of receive elements, each receive element of the plurality of receive elements serving as a receive channel.

18. The magnetic resonance installation of claim 17, wherein the plurality of receive elements include at least 32 receive elements.

19. The coil facility of claim 1, wherein the first receiver and the second receiver are simultaneously transposable by the actuator system between the first setting and the second setting, such that as the first receiver is arranged into the examination space the second receiver is arranged out of the examination space, and as the second receiver is arranged into the examination space the first receiver is arranged out of the examination space.

20. The magnetic resonance installation of claim 11, wherein the first receiver and the second receiver are simultaneously transposable by the actuator system between the first setting and the second setting, such that as the first receiver is arranged into the examination space the second receiver is arranged out of the examination space, and as the second receiver is arranged into the examination space the first receiver is arranged out of the examination space.

\* \* \* \* \*